(12) United States Patent
Ullah et al.

(10) Patent No.: US 9,137,999 B1
(45) Date of Patent: Sep. 22, 2015

(54) PESTICIDAL COPPER COMPOSITIONS AND METHODS FOR USING THE SAME

(71) Applicant: SePRO Corporation, Carmel, IN (US)

(72) Inventors: Hamid Ullah, Whitakers, NC (US); West Bishop, Nashville, NC (US); Bill Whitford, Chapel Hill, NC (US)

(73) Assignee: SePro Corporation, Indianapolis, IN (US)

( * ) Notice: Subject to any disclaimer, the term of this patent is extended or adjusted under 35 U.S.C. 154(b) by 0 days.

(21) Appl. No.: 13/778,795

(22) Filed: Feb. 27, 2013

(51) Int. Cl.
    *A01N 55/02*     (2006.01)

(52) U.S. Cl.
    CPC ........................................ *A01N 55/02* (2013.01)

(58) Field of Classification Search
    None
    See application file for complete search history.

(56) References Cited

U.S. PATENT DOCUMENTS

| | | |
|---|---|---|
| 2,734,028 A | 2/1956 | Domogalla |
| 3,765,864 A | 10/1973 | Kerst et al. |
| 3,930,834 A | 1/1976 | Schulteis et al. |
| 4,030,907 A | 6/1977 | McNall |
| 4,098,602 A | 7/1978 | Seymour et al. |
| 4,324,578 A | 4/1982 | Seymour et al. |
| 4,361,435 A | 11/1982 | Meyers et al. |
| 4,398,937 A | 8/1983 | van Aller et al. |
| 4,505,734 A | 3/1985 | Freedenthal et al. |
| 5,407,899 A | 4/1995 | Howell |
| 6,069,113 A | 5/2000 | Kierzkowski et al. |
| 6,245,381 B1 * | 6/2001 | Israel ............................ 427/186 |
| 2006/0134239 A1 * | 6/2006 | Weide et al. .................. 424/745 |

OTHER PUBLICATIONS

Könnecker et al., Environmental properties and aquatic hazard assessment of anionic surfactants: Physico-chemical, environmental fate and ecotoxicity properties, Ecotoxicology and Environmental Safety 74: 1445-1460 (2011).*

Cutrine® Ultra label dated Aug. 1, 2012 [Downloaded from the internet on Mar. 19, 2014 from http://pdf.tirmsdev.com/Web/13/43785/13_43785_LABEL_English_.pdf?download=true].*

* cited by examiner

*Primary Examiner* — Robert A Wax
*Assistant Examiner* — Thor Nielsen
(74) *Attorney, Agent, or Firm* — Woodard, Emhardt, Moriarty, McNett & Henry LLP

(57) ABSTRACT

Compositions useful in pesticidal applications include water, a copper complex and an alpha olefin sulfonate surfactant. Additional components can be included in such formulations including one or more additional surfactants, and one or more penetrating agents.

21 Claims, 2 Drawing Sheets

PESTICIDAL COPPER COMPOSITIONS AND METHODS FOR USING THE SAME

BACKGROUND

The present invention relates generally to copper-containing compositions and methods that are useful, for example, in herbicidal, fungicidal, bactericidal, algaecidal or other pesticidal applications.

As background to the present disclosure, aquatic organisms very commonly arise as undesired pests in waters and wetlands of the United States of America and elsewhere. Examples include cyanobacteria, planktonic algae, filamentous algae, and macroalgae (*Chara, Nitellopsis, Nitella, Bangia* and *Tolypella*). These pests often present problems in ponds, lakes, and other water bodies such as: degrade aesthetics, decrease property values, clog irrigation intakes, produce off flavor taste/smell to drinking water/fish, disrupt ecological integrity, create health concerns through toxin production and impede fishing/recreational activities.

Copper has been used in the control of aquatic weeds, fungi, and algae. Commercially, copper algaecides are available as liquid formulations of dissolved copper salts and complexes of copper salts. Formulations of copper-based algaecides differ and formulation advancements in some cases are designed to enhance the affinity and efficacy for targeted algae management. Since efficacy of copper algaecides is manifested after transfer of copper into the cell, development of formulations that increase penetration would be advantageous because they can provide a greater degree of control with lower amounts of product.

Formulation stability is another key factor in the successful development of formulations. The development of storage-stable, flowable liquid formulations has presented many difficulties over the years. Attempts to prepare such formulations meet with a variety of failures, commonly involving phase separation and/or an inhomogeneous distribution of the copper or other active component(s) of the formulation. In view of the background in this area, needs exist for improved and/or alternative formulations of copper pesticidal agents.

SUMMARY

In certain aspects, the present invention provides compositions that include a copper complex, an alpha olefin sulfonate surfactant, and water. Such compositions can deliver copper in a highly effective manner when applied (alone or combined with another material such as another liquid medium) to algae, plants, fungi, bacteria or growth-supporting environments of the same, such as a body of water, soil, or a soil surface where pesticidal activity is desired. Application of the preferred compositions as describe herein can in certain embodiments lead to rapid uptake and efficacy of copper as a pesticidal agent.

In one aspect, the invention provides a pesticidal composition that includes a copper complex, one or more alpha olefin sulfonate surfactants, and water. The compositions can optionally include one or more additional surfactants, algaecides, other pesticides (e.g., herbidcides, insecticides, fungicides), dyes, stabilizers (e.g., butylated hydroxy toluene), fragrances, viscosity-modifying additives, suspension aids, dispersants, and others.

In additional aspects of the invention, provided are methods for treating surfaces or environments with copper, comprising applying to them a composition as described herein, or another composition prepared therefrom, e.g., by combining the composition with another substance such as an aqueous or other liquid medium. In certain preferred modes these methods are for controlling aquatic algae in a body of water, and the composition, or any other composition prepared by combining the composition with an aqueous or other liquid medium, is added to the body of water. Such addition can be accomplished in any suitable manner including injection or spraying of the composition or other composition into the body of water.

Additional embodiments of the invention, as well as features and advantages thereof, will be apparent from the descriptions herein.

DETAILED DESCRIPTION

Figure 1:
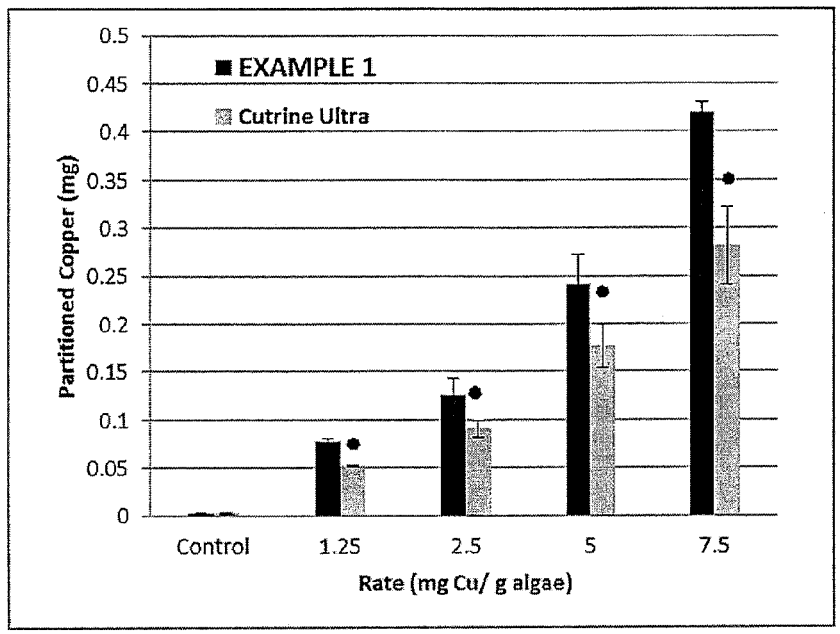
FIG. 1 provides a graph showing a comparison of partitioned copper (algae bio-concentration) to *Pithophora varia* following 7 day exposures to the formulation of EXAMPLE 1 and the commercial product Cutrine Ultra. Error bars represent one standard deviation. Asterisks represent significant differences ($\alpha=0.1$).

For the purposes of promoting an understanding of the principles of the invention, reference will now be made to certain embodiments and specific language will be used to describe the same. It will nevertheless be understood that no limitation of the scope of the invention is thereby intended, such alterations and further modifications, and such further applications of the principles of the invention as described herein being contemplated as would normally occur to one skilled in the art to which the invention relates.

Copper is a known pesticidal agent. For example, it is known for use as an algaecide, an herbicide, a bactericide and a fungicide. Copper can be included in the compositions of the present invention in any suitable pesticidal amount. Copper amounts of at least 0.1% by weight in the composition, and/or copper amounts no greater than about 25% by weight of the composition, are contemplated in certain aspects of the invention. In regard to these weight percentages and the other weight percentages stated herein, the percentages are given as weight:weight percentages, unless stated otherwise or clear from context. Also, for copper weight percentages given herein, the copper is considered as metal.

In additional embodiments herein, copper is included in the composition in the range of about 3% by weight to about 15% by weight, preferably about 3% by weight to about 11% by weight, more preferably about 5% by weight to about 10% by weight. In certain embodiments, copper is included in the composition in an amount of about 7% by weight to about 10% by weight.

In aspects of the present disclosure, a water-soluble salt of copper can be complexed with one or more alkanolamines in the composition. Such complexation can help to prevent the precipitation of copper in waters containing carbonates and bicarbonates, which precipitation may decrease uptake by target pests or deleteriously effect exposure time or selectivity for a target pest. Alkanolamines suitable for use include, but are not limited to monoalkanolamines such as monoethanolamine, dialkanolamines such as diethanolamine, and trialkanolamines such as triethanolamine. Typically, the one or more alkanolamines are included in molar excess relative to the copper. In certain embodiments the alkanolamine(s) is/are present in the pesticidal composition in an amount from about 0.1% by weight to about 75% by weight. More preferably, the alkanolamine(s) is/are present in amounts from about 0.1% by weight to about 50% by weight of the final pesticidal composition. The copper complex itself can, in certain embodiments, constitute at least about 5% by weight of the composition and/or no more than about 50% by weight of the pesticidal composition, an in some embodiments about 10% to about 40% by weight of the composition.

Additionally, the one or more alkanolamines may include a mixture of one or more of monoalkanolamines such as monoethanolamine, dialkanolamines such as diethanolamine, or trialkanolamines such as triethanolamine. In some embodiments, the molar ratio of triethanolamine to copper ranges from about 5:1 to about 0.5:1. In another embodiment, the molar ratio of triethanolamine to copper ranges from about 3:1 to about 1:1. In yet another embodiment, the molar ratio of triethanolamine to copper is about 1:1. In one embodiment, the molar ratio of monoethanolamine to copper ranges from about 5:1 to about 0.5:1. In another embodiment, the molar ratio of monoethanolamine to copper ranges from about 3:1 to about 0.5:1. In yet another embodiment, the molar ratio of monoethanolamine to copper is about 2.5:1. Monoethanolamine and triethanolamine can be used in combination in the composition, in certain forms with each occurring relative to copper in any of the above-specified ranges.

In addition to the copper complex, pesticidal compositions of the present disclosure include a carrier that comprises one or more α-olefin sulfonate surfactants. In this regard, α-olefin sulfonates are a class of surfactants typically prepared by reacting linear α-olefins (terminal olefins) with $SO_3$, although branched α-olefins may be used as well. α-Olefin sulfonates can be included in a variety of chain lengths, and are typically provided commercially as a composition that includes a mixture of α-olefin sulfonates of different chain lengths, although isolated or purified compositions including essentially α-olefin sulfonate molecules of only a single chain length may also be used. In one embodiment of the invention the α-olefin sulfonates are included with linear carbon chain lengths within the range of about 4 carbons to about 20 carbons. In another embodiment, the α-olefin sulfonate(s) is/are included with linear carbon chain length(s) in the range of about 8 to about 20. In yet another embodiment, the α-olefin sulfonate(s) is/are included with linear carbon chain length(s) in the range of about 12 to about 20. Most preferably, the α-olefin sulfonate(s) is/are included with linear carbon chain length(s) of about 14 to about 16. α-Olefin sulfonate(s) may be included in embodiments of the present invention in amounts of no less than about 0.1% by weight and no greater than about 50% by weight. In other embodiments, α-olefin sulfonate(s) is/are present in amounts of no less than about 0.1% and no greater than about 25% by weight. In some other embodiments, α-olefin sulfonate(s) is/are present in amounts of no less than about 0.1% by weight and no greater than about 20% by weight of the compositions. In yet other embodiments, α-olefin sulfonate(s) is/are present in amounts of no less than about 0.1% by weight and no greater than about 15% by weight. In certain preferred embodiments, α-olefin sulfonate(s) is/are present in amounts of no less than about 0.1% by weight and no greater than about 10% by weight of the compositions.

In addition to α-olefin sulfonate surfactant(s) present in the compositions of the present invention, one or more additional surfactants may be included. These additional surfactants may include, for example, anionic, neutral, or cationic surfactants. Common anionic surfactants include, but are not limited to olefin sulfonates, alkyl sulfonates, alkyl sulfates, calcium sulfate, long chain fatty acid salts, phosphoric and polyphosphoric acid esters among others. Common neutral or nonionic surfactants include, but are not limited to long chain carboxylic acid esters, ethoxylated castor oil, alkanolamine condensates, polyoxyethylnated alkylphenols, polyoxyethylenated alcohols, and polyoxyethylenated glycols. Common cationic surfactants include, but are not limited to long chain amines and their salts, acylated amines and their salts, quaternary ammonium salts, and amine oxides among others. Still other surfactants may be used including as examples tall oil fatty acids, alcohol ethoxylates, alkylphenol exthoxylates, and the like.

The carrier can also include one or more ingredients of which aid the penetration of the active copper complex into the algae or other pest, or surface or environment, to be treated. Suitable penetrating agents include, but are not limited to, hydrocarbons, diesel fuel, kerosene, dimethylsulfoxide, vegetable oils, methlylated seed oils, alcohols including but not limited to ethanol, propanol, octanol, ethyl acetate, terpenes and terpene derivatives. Common terpene penetrating agents include, but are not limited to, limonene including d-limonene, 1-limonene, and d/l-limonene. In certain embodiments of the present invention limonene, such as d-limonene, is present from about 0.1% by weight in the herbicidal composition to about 25% by weight of the herbicidal composition. Typically, limonene, such as d-limonene, is included in the range of about 0.1% by weight to about 15% by weight. More preferably, limonene, such as d-limonene, is present in amount from about 3% by weight to about 10% by weight. In certain embodiments, limonene, such as d-limonene, is present in an amount of about 3% by weight to about 7% by weight.

Additional ingredients in the pesticidal composition may include, for example, one or more surfactants, one or more algaecides, other pesticides (e.g., herbicides, insecticides), dyes, stabilizers (e.g., butylated hydroxy toluene), fragrances, viscosity-modifying additives, suspension aids, dispersants, and others.

Besides water, the copper complex, and the one or more α-olefin sulfonate surfactants, the remainder of the additional ingredients, when present, typically together constitute a relatively low percentage by weight of the pesticidal composition, for example from about 0.1% by weight to about 25% by weight of the composition. More preferably, these additional ingredients other than water, the copper complex and the one or more α-olefin sulfonate surfactants, comprise from about 0.1% by weight to about 20% by weight of the composition.

The ingredients of the algaecidal composition can be conventionally combined, with preference to form a homogenous solution or other mixture. Conventional equipment as well as heating and agitating conditions, as necessary, can be employed. The formation of storage stable solutions, for example those that exhibit the capacity to remain homogenous solutions with uniform copper concentrations and/or without any phase separation for a period of at least 30 days and more preferably at least a year when maintained at 25° C. in a stationary condition, are preferred. Such maintenance over time will typically be in a sealed, fluid-tight inert container.

Compositions and methods of the disclosure may be used, for example, in the complete or partial control of noxious pests in or on terrestrial or aquatic environments, animals, or surfaces, among other uses. In certain aspects, algae and cyanobacteria for control herein include, for example, those of the genera: *Achnanthes, Anabaena, Anabaenopsis, Anacystis, Ankistrodesmus, Aphanizomenon, Aphanocapsa, Aphanothece, Arthrospira, Asterionella, Audouinella, Aulacoseira, Bangia, Batrachospermum, Bulbochaete, Calothrix, Carteria, Ceratium, Chamaesiphon, Chara, Chlamydobotrys, Chlamydomonas, Chlorella, Chlorococcum, Chromulina, Chroococcus, Cladophora, Closterium, Cocconeis, Coelastrum, Coelosphaerium, Coleodesmium, Compsopogon, Crysococcus, Cyclotella, Cylindrocapsa, Cylindrospermopsis, Cylindrospermum, Cymbella, Desmidium, Diatoma, Dictyosphaerium, Didymosphenia, Dinobryon, Draparnaldia, Euastrum, Eudorina, Euglena, Fragilaria, Gloeocapsa, Gloeotrichia, Gomphonema, Gomphosphaeria, Gonium, Hapalosiphon, Haematococcus, Homoeothrix, Hydrodictyon, Lemanea, Lepocinclis, Leptolyngbya, Limnothrix, Lyngbya, Mallomonas, Melosira, Meridion, Merismopedia, Micractinium, Micrasterias, Microcoleus, Microcystis, Microspora, Mougeotia, Navicula, Nitella, Nitellopsis, Nitzschia, Nodularia, Nostoc, Oedogonium, Oocystis, Oscillatoria, Palmella, Pandorina, Pediastrum, Peridinium, Phacotus, Phacus, Phormidium, Pinnularia, Pithophora, Pfiesteria, Planktolyngbya, Planktothrix, Plectonema, Porphyrosiphon, Prymnesium, Pseudanabaena, Raphidiopsis, Rhizoclonium, Rhodomonas, Rivularia, Schizothrix, Scenedesmus, Scytonema, Sphaerocystis, Spirogrya, Staurastrum, Stauroneis, Stephanodiscus, Stigeoclonium, Surirella, Synechococcus, Synechocystis, Synedra, Synura, Tabellaria, Tetraedron, Tetraspora, Tolypella, Tolypothrix, Trachelomonas, Tribonema, Trichocoleus, Trichodesmium, Tychonema, Ulothrix, Umezekia, Uroglenopsis, Volvox, Westella,* and/or *Zygnema*. More specifically, target algae include *Hydrodictyon* spp., *Pithophora* spp., *Lyngbya* spp., *Planktothrix* spp., *Oscillatoria* spp., *Nitella* spp., *Chara* spp., *Phormidium* spp., *Microcystis* spp., *Anabaena* spp., *Aphanizomenon* spp., and/or *Nodularia* spp.

When the compositions of the present disclosure are used as aquatic algaecides or herbicides, bodies of water to be treated with the present invention will typically be fresh water bodies such as ponds, lakes, wetlands, reservoirs, rivers or irrigation canals, although other bodies of water may also be treated in accordance with this invention. The compositions can be added to the bodies of water in any suitable manner, including surface addition (e.g., spraying, drip) and/or sub-surface addition (e.g., injection). As well, the compositions of the invention can be applied "as is" to bodies of water, plants, or to terrestrial or other environments or surfaces to be treated, or can be diluted by combination with another material such as a liquid material, typically an aqueous liquid material (e.g., water), and/or with another algaecide or algaecidal formulation, prior to application. Such dilutions may be undertaken for example when compositions of the invention are provided as concentrates.

When treating other environments or surfaces with compositions of the invention, they can be applied in any suitable manner. As examples, injection, spraying, brushing, flushing, immersion, or other techniques, can be used to apply compositions of the invention for pesticidal or other purposes. In such applications, preferred compositions of the invention will be stable solutions, which will benefit both their storage and their ease and consistency of application.

In order to promote a further understanding of the present invention and its various embodiments, the following specific examples are provided. It will be understood that these examples are illustrative and not limiting of the invention.

Example 1

Composition Preparation

A solution of the active copper complex is first prepared by mixing 163 pounds copper carbonate, 200 pounds triethanolamine, 200 pounds monoethanolamine, and 270 pounds water until homogenous. A carrier composition is then prepared by mixing 57 pounds d-limonene, 10 pounds calcium sulfonate, 30 pounds ethoxylated castor oil, 0.2 pounds butylated hydroxytoluene, and 2 pounds anti-foaming agent "polydimethylsiloxane emulsion". 98 pounds sodium α-olefin sulfonate is then added to the solution of the active copper complex and mixed until homogenous. The carrier composition is then added and mixed until homogenous to give the final composition.

Example 2

Stability of Formulation of Example 1

Materials and Methods:

The stability of formulations is observed by removing 5 mL aliquots of the formulations at the top one inch of the formulation in a container, and at the bottom one inch of the formulation from the same sealed, fluid-tight inert container and measuring the density (using a Densito 30PX instrument, manufactured by Metier Toledo). The two density measurements are compared. If the two measurements are within +5% or −5% of each other, the formulation is considered to be stable and indicate the lack of phase separation. An additional desired component to copper based pesticides is maintaining the targeted copper concentration in a homogenous state. Measurements of copper concentration were also measured for formulations of Example 1 and considered stable if the formulation 1) maintains a homogenous copper concentration top to bottom measured by having values within +5% or −5% of each other and 2) maintains the targeted copper concentration in both the top and bottom of the container by having values within +5% or −5% of the targeted copper level. Copper was measured by diluting a specific mass of the concentrated EXAMPLE 1 formulation in deionized water and acidifying with trace metal grade nitric acid to 2% v/v. Samples were measured using inductively coupled plasma-optical emission spectrometry (Shimadzu ICPE 9000) using appropriate calibration standards and quality control checks according to Standard Operating Procedures. Phase separation and copper content were measured in different sizes of sealed, fluid-tight inert containers for example containing from about 1 gallon up to 275 gallons. Measurements were taken initially meaning immediately after filling of containers and monthly thereafter, without disturbing, for total of six months.

Results:

The stability of the formulation of EXAMPLE 1 was measured over time as described above. The formulation of EXAMPLE 1 was determined to be stable for greater than six months when maintained at 25° C. in a stationary condition. The formulation of EXAMPLE 1 was determined to maintain a homogenous copper concentration as well as the targeted copper concentration for greater than six months when maintained at 25° C. in a stationary condition.

Example 3

Efficacy of Composition of Example 1

Materials and Methods:
Testing and Culture Conditions:

The filamentous alga used in these experiments was collected from a reservoir. The sample was dominated by one species identified as Pithophora varia Wille using light microcopy (Wehr and Sheath 2003, Prescott 1970). P. varia was cultured and tested in a controlled environment (temperature of 23±1° C. and a 16 hour light/8 hour dark photoperiod illuminated by fluorescence lighting at an intensity of 3100±100 lux.; Lewis, et al. 1994) using well water which resembled site water characteristics (pH 7±1.5, DO 8±1 mg $O_2$/L, temperature 23±2° C., conductivity 130-350 µS/cm², alkalinity 80-110 mg $CaCO_3$/L, hardness 90-120 mg $CaCO_3$/L; APHA 2005). The planktonic alga used in these experiments, Scenedesmus dimorphus Kutz, was attained from the University of Texas at Austin culture collection (UTEX 1237). S. dimorphus was cultured and tested in BG-11 nutrient media (Berberoglu, et al. 2008) under similar environmental conditions outlined above.

Experimental Design

The mass of P. varia in each treatment was held constant at 0.1 g±0.01 g wet weight and exposed to a series of aqueous copper concentrations targeting background, 0.25, 0.5, 0.75, and 1.0 mg Cu/L as Cutrine®-Ultra, the composition of EXAMPLE 1 and copper sulfate pentahydrate granules in 500 mL flasks containing 250 mL water in seven day toxicity tests. S. dimorphus was tested upon achieving densities of 1.5×10⁶ cells/mL to allow continued growth in controls and concomitant ability to measure significant differences in responses. Copper concentrations in S. dimorphus exposures included background, 0.25, 0.5, 0.75, and 1.0 mg Cu/L as Cutrine®-Ultra, EXAMPLE 1 and copper sulfate pentahydrate in 500 mL flasks containing 250 mL water in four day toxicity tests. Stock algaecide solutions (1000 ppm elemental copper) were prepared within four hours of test initiation in NanoPure™ water and serial dilutions were used to obtain treatment copper concentrations. Six replicates of each exposure concentration were tested for each algaecide along with six untreated controls. Three replicates were randomly selected for response analyses and three were used for copper measurements.

Algae Response: Filament/Cell Viability

Percent filament viability was measured by taking 0.05 g of P. varia from 3 replicates of each treatment and untreated control and immersing in 5 mL 0.1% Methylene Blue for approximately 10 minutes. As a mortal stain, cells that allow entry of methylene blue are considered dead (Corradi and Gorbi 1993). 100 filaments per replicate were randomly selected and examined and the percent mortality was determined by the proportion that were internally stained bright blue. Planktonic cell viability was determined by adding Methylene Blue to homogenized S. dimorphus exposure vessels targeting a final concentration of 0.1%. Counts of viable cells (not stained blue) were conducted following 5 minutes of exposure. Cell densities were measured using an improved neubauer hemocytometer (Hausser Scientific Co. Horsham, Pa. 19044).

Algae Response: Chlorophyll Content

Algal chlorophyll α was measured on three initial samples and three replicates of each treatment and untreated controls. Due to the robust structure of P. varia, chlorophyll analysis was modified from standard methods by freezing the 0.05 g sample (−12° C.) for a minimum of 24 h. 20 mL of homogenized S. dimorphus treatments were filtered (0.45 µm nitrocellulose) and used to calculate chlorophyll α concentrations. Each sample was placed in 5 mL buffered acetone and sonicated to lyse cells (modified APHA 2005). Chlorophyll a was measured fluorometrically using a Wallac Victor² spectrofluorometer by correlating with a matrix-matched standard calibration curve (10-640 ug/L; Sigma C-5753); samples were diluted in same matrix if needed for measurement to be within the standard curve.

Copper Sorption and Critical Burden Measurements

The amount of copper absorbed by and adsorbed to the algae was measured in 5 initial samples to determine background levels and three replicates of each treatment and untreated controls. Adsorbed copper was measured by rinsing 0.1 g wet weight P. varia with 10 mL of 2 mM EDTA for 10 minutes to remove adhered metal ions from surface then filtering through a clean 0.2 µm glass fiber filter Adsorbed copper was measured on S. dimorphus by gently filtering 50 mL of homogenized exposure solution through an acid washed (10% $HNO_3$) 0.45 µm nitrocellulose filter, then rinsing with 10 mL of 2 mM EDTA for 10 minutes, filtering and collecting filtrate for analysis. Absorbed copper was measured by taking the rinsed algae and digesting in 2 mL 70% trace metal grade nitric acid ($HNO_3$ purchased from Fisher Scientific, Inc. A509, 2 mL of 30% $H_2O_2$ and 6 mL NanoPure™ water and microwave at 180° C. until clear (Tripathi, et al. 2006; USEPA 1996). Aqueous dissolved copper concentrations were measured by taking 50 mL of exposure solution, filtering, then acidifying to 1% with trace metal grade nitric acid. Copper was measured using inductively coupled plasma-optical emission spectrometry (Shimadzu ICPE 9000) using a matrix-matched calibration curve from serial dilution of a 1000 ppm copper standard (Fisher Scientific, Inc. SC194; APHA 2005). The limit of detection for copper was 1 µg/L (0.1 µg Cu/g algae). The lowest concentration of absorbed copper at which control was achieved (i.e., significant reduction in chlorophyll α content/cell viability, $EC_{75}$) for each algaecide, was identified as the critical burden in units of mg copper per gram of algae. Mass fractions of copper were calculated based upon sorbed fractions and water column concentration (times volume).

Copper Algaecide Formulation Efficiency

The algae bio-concentration factor was used to compare affinities of different copper formulations to the algae and was calculated by the equation ABcF=([Cu] adsorbed+absorbed to algae)/[Cu] dissolved in water). The copper formulation efficiency was further compared based upon proportion of copper absorbed compared with copper adsorbed and total applied. This algae bio-absorption factor was calculated by the equation ABaF=[Cu] absorbed/([Cu] adsorbed+[Cu] in water). Correlating algae bio-absorption factors with the critical burden measurements provides data on the lowest rate of copper that should be applied to attain the critical burden.

Figure 2:
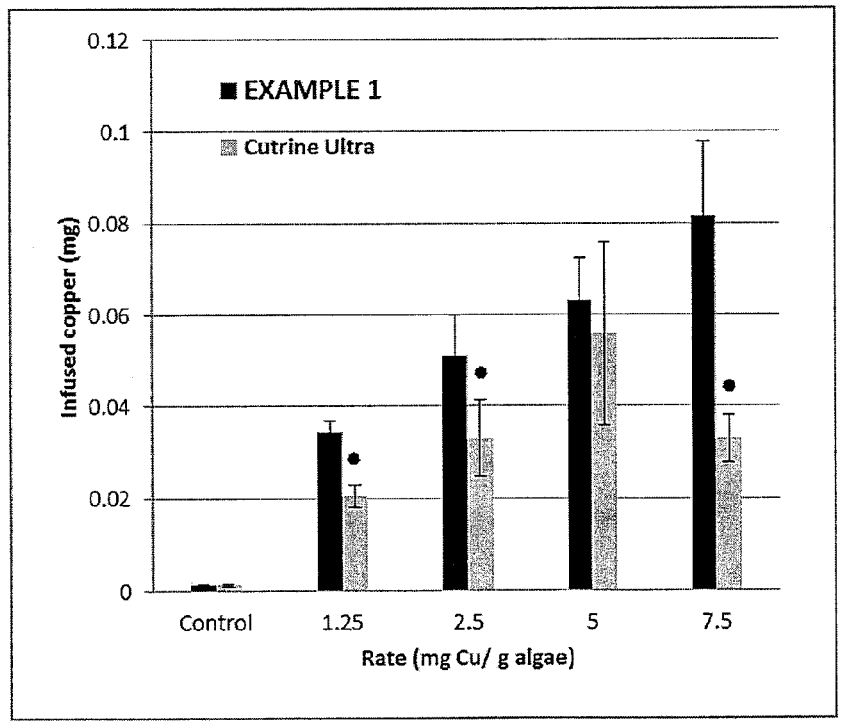
FIG. 2 provides a graph showing a comparison of internalized copper in *Pithophora varia* following 7 day exposures to the formulation of EXAMPLE 1 and Cutrine Ultra. Error bars represent one standard deviation. Asterisks represent significant differences ($\alpha=0.1$).
Figure 3:
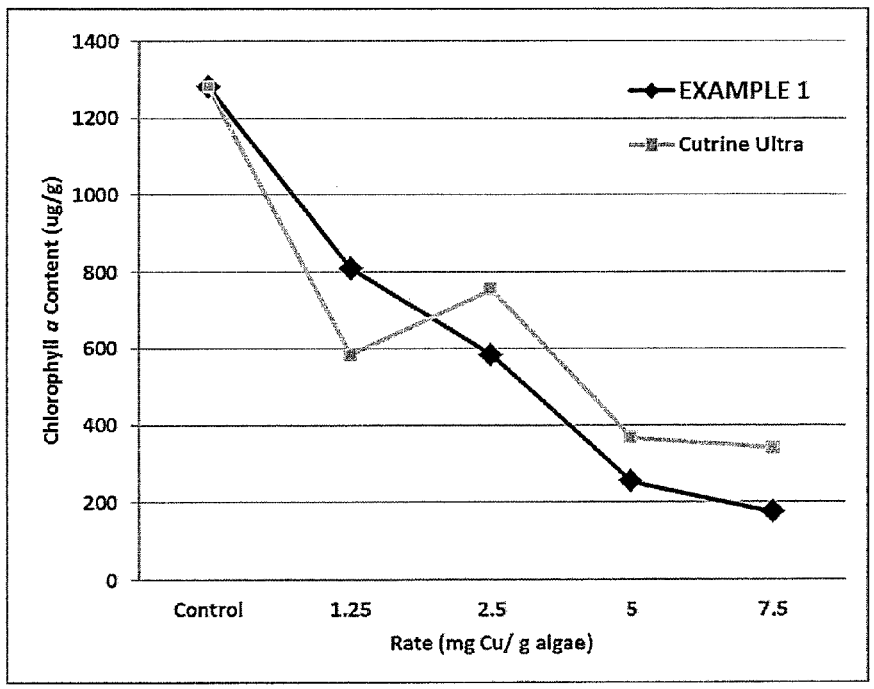
FIG. 3 provides a graph showing a comparison of *Pithophora varia* chlorophyll $\alpha$ content following 7 day exposures to the formulation of EXAMPLE 1 and Cutrine Ultra.
Figure 4:
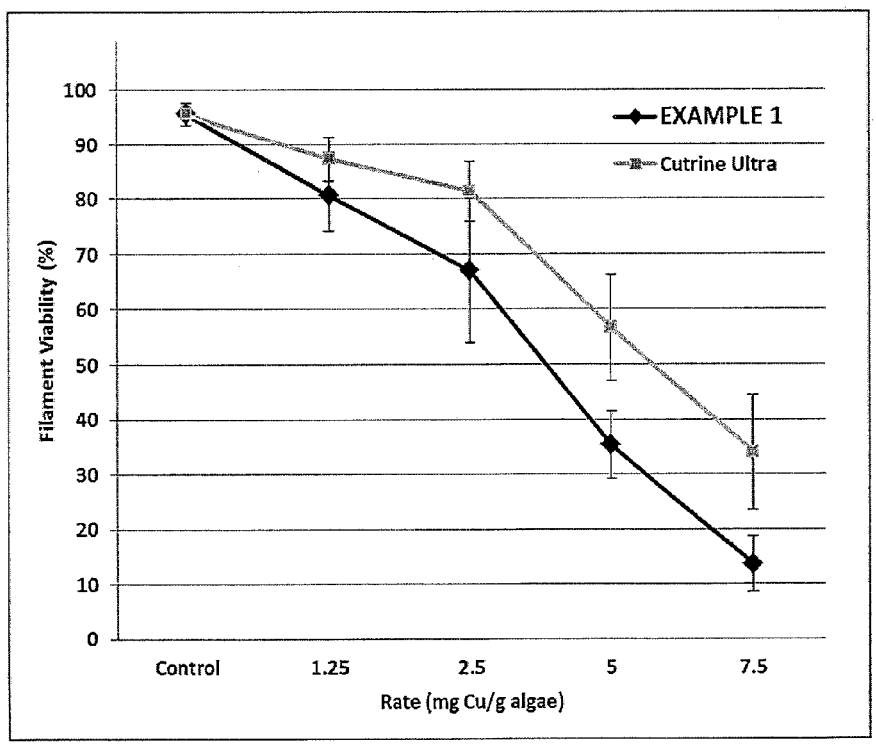
FIG. 4 provides a graph showing a comparison of *Pithophora varia* filament viability following 7 day exposures to the formulation of EXAMPLE 1 and Cutrine Ultra. Error bars represent one standard deviation.

Results:

At every corresponding concentration of copper tested, EXAMPLE 1 had increased copper partitioning and absorption into the algae biomass as compared with Cutrine®-Ultra. Overall copper partitioning of the EXAMPLE 1 formulation was significantly different (α=0.1) at every concentration tested (1.25, 2.5, 5, and 7.5 mg Cu/g algae) with p-values of 0.00015, 0.03718, 0.05804, and 0.00424, respectively (FIG. 1). In terms of absorbed copper, significant differences (α=0.1) were measured at the 1.25, 2.5 and 7.5 mg Cu/g algae rates with p-values of 0.00255, 0.06176 and 0.00761, respectively (FIG. 2). The average copper absorption efficiency was 36% greater in EXAMPLE 1 exposures compared with Cutrine®-Ultra exposures. Concomitantly, the efficacy toward the targeted algae was observed at lower exposure rates of EXAMPLE 1, due to the efficiency of achieving the critical burden (internal threshold copper level that elicits control). Differences were also discerned in exposure-response relationships for both chlorophyll and filament viability analyses (FIGS. 3 and 4). EXAMPLE 1 elicited 1) increased copper affinity to algae, 2) increased copper absorption into the algae, 3) increased algaecidal control efficacy; as compared with Cutrine®-Ultra at similar rates. The formulation of EXAMPLE 1 had proportionally increased uptake rates with increasing exposures, supporting a passive infusion concept independent of algae activity, protective cells, mucilage, structural character, defense mechanisms, and integrity of uptake channels.

The uses of the terms "a" and "an" and "the" and similar references in the context of describing the invention (especially in the context of the following claims) are to be construed to cover both the singular and the plural unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A pesticidal composition, comprising:
copper complexed with one or more alkanolamines;
one or more alpha olefin sulfonate surfactants;
limonene; and
water; and
wherein copper is present in an amount of about 5% to about 10% by weight of the composition; and
wherein said composition is homogenous and does not exhibit phase separation for at least 30 days when maintained at 25° C. in a stationary condition; and
wherein the one or more alpha olefin sulfonate surfactants are present in an amount of about 0.1 to about 15% by weight of the composition.

2. The composition of claim 1, wherein:
said one or more alpha olefin sulfonate surfactants comprise a linear carbon chain in the range of about 4 to about 20 carbon atoms.

3. The composition of claim 1, wherein:
the one or more alpha olefin sulfonate surfactants are present in an amount of about 0.1 to about 10% by weight of the composition.

4. The composition of claim 1, wherein:
the one or more alpha olefin sulfonate surfactants are present in an amount of about 0.1 to about 5% by weight of the composition.

5. The composition of claim 1, wherein:
copper is present in an amount of about 7% to about 10% by weight of the composition.

6. The composition of claim 1, wherein:
said one or more alpha olefin sulfonate surfactants comprise a linear carbon chain in the range of about 4 to about 20 carbon atoms.

7. The composition of claim 1, wherein:
said one or more alpha olefin sulfonate surfactants comprise a linear carbon chain in the range of about 8 to about 20 carbon atoms.

8. The composition of claim 1, wherein:
said one or more alpha olefin sulfonate surfactants comprise a linear carbon chain in the range of about 12 to about 20 carbon atoms.

9. The composition of claim 1, wherein:
said one or more alpha olefin sulfonate surfactants comprise a linear carbon chain in the range of about 14 to about 20 carbon atoms.

10. The composition of claim 1, wherein:
said one or more alpha olefin sulfonate surfactants comprise a linear carbon chain in the range of about 14 to about 16 carbon atoms.

11. A composition, comprising:
copper complexed with one or more alkanolamines;
one or more alpha olefin sulfonate surfactants;
one or more additional surfactants selected from the group consisting of anionic, nonionic, or cationic surfactants;
water;
wherein said composition is homogenous and does not exhibit phase separation for at least 30 days when maintained at 25° C. in a stationary condition; and
wherein the one or more alpha olefin sulfonate surfactants are present in an amount of about 0.1 to about 15% by weight of the composition.

12. The composition of claim 11, wherein:
the one or more additional surfactants include a hydroxyalkane sulfonate surfactant.

13. The composition of claim 11, wherein the copper complexed with one or more alkanolamines constitutes at least about 5% by weight of the composition.

14. The composition of claim 13, wherein the copper complexed with one or more alkanolamines constitutes no more than about 50% by weight of the composition.

15. The composition of claim 14, wherein the copper complexed with one or more alkanolamines constitutes about 10% to about 40% by weight of the composition.

16. The composition of claim 11, also comprising d-limonene, 1-limonene, or a combination thereof.

17. A method of controlling the growth of algae comprising the step of adding to a body of water an algaecidally effective amount of the composition of claim 1.

18. The method of claim 17, wherein the algae to be treated include one or more of *Hydrodictyon* spp., *Pithophora* spp., *Lyngbya* spp., *Oscillatoria* spp., *Nitella* spp., *Chara* spp., *Phormidium* spp., *Microcystis* spp., *Anabaena* spp., *Aphanizomenon* spp., *Nodularia* spp.

19. A method for treating a surface or environment comprising applying to the surface or environment (i) a composition of claim 1, or (ii) a composition prepared by combining a composition of claim 1 with another substance.

20. The method of claim 19, wherein said another substance is an aqueous liquid medium.

21. The method of claim 19, which is a method for algaecidally treating an aquatic environment.

* * * * *